US008282936B2

(12) United States Patent
Sasagawa et al.

(10) Patent No.: US 8,282,936 B2
(45) Date of Patent: Oct. 9, 2012

(54) HUMAN PAPILLOMAVIRUS VACCINE FOR ORAL ADMINISTRATION

(75) Inventors: Toshiyuki Sasagawa, Kanazawa (JP); Hideki Tohda, Yokohama (JP); Yuko Hama, Yokohama (JP)

(73) Assignees: Asahi Glass Company, Ltd., Tokyo (JP); National University Corporation Kanazawa University, Kanazawa-shi (JP)

( * ) Notice: Subject to any disclaimer, the term of this patent is extended or adjusted under 35 U.S.C. 154(b) by 151 days.

(21) Appl. No.: 12/116,501

(22) Filed: May 7, 2008

(65) Prior Publication Data

US 2009/0017063 A1 Jan. 15, 2009

Related U.S. Application Data

(60) Division of application No. 11/684,062, filed on Mar. 9, 2007, now abandoned, which is a continuation of application No. PCT/JP2005/016638, filed on Sep. 9, 2005.

(30) Foreign Application Priority Data

Sep. 10, 2004 (JP) ................. 2004-263580

(51) Int. Cl.
*A61K 39/00* (2006.01)
*C12N 1/19* (2006.01)
(52) U.S. Cl. .............. 424/204.1; 435/254.2; 435/69.1
(58) Field of Classification Search .............. None
See application file for complete search history.

(56) References Cited

U.S. PATENT DOCUMENTS

| | | | |
|---|---|---|---|
| 5,871,742 A | | 2/1999 | Saitoh et al. |
| 6,153,201 A | | 11/2000 | Rose et al. |
| 6,210,663 B1 | * | 4/2001 | Ertl .................. 424/93.2 |
| 6,228,368 B1 | | 5/2001 | Gissmann et al. |
| 6,613,557 B1 | | 9/2003 | Frazer et al. |
| 6,908,613 B2 | * | 6/2005 | Wilson et al. ........ 424/192.1 |
| 2005/0075298 A1 | * | 4/2005 | Chen et al. ............ 514/44 |

FOREIGN PATENT DOCUMENTS

| | | |
|---|---|---|
| JP | 10-506791 | 7/1998 |
| JP | 10-507916 | 8/1998 |
| JP | 2001-519161 | 10/2001 |
| JP | 2002-510976 | 4/2002 |
| JP | 2002-516291 | 6/2002 |
| JP | 2003-520188 | 7/2003 |
| JP | 2004-269 | 1/2004 |
| JP | 2004-121263 | 4/2004 |
| WO | WO 96/12801 | 5/1996 |
| WO | WO 99/01557 | 1/1999 |
| WO | WO 00/09671 | 2/2000 |
| WO | WO 2004/058157 A2 | 7/2004 |

OTHER PUBLICATIONS

Sasagawa et al (Virology, 1995, vol. 206, p. 126-135, IDS of Feb. 12, 2009).*
Sasagawa et al (Virus Research Mar. 8, 2005, vol. 110, p. 81-90 in IDS on May 7, 2008).*
Warzecha et al. (Journal of Virology, 2003, vol. 77, p. 8702-8711 in IDS on May 7, 2008).*
Koutsky et al. (The New England Journal of Medicine, 2002, vol. 347, p. 1645-1651 in IDS on May 7, 2008).*
M. P. Schreuder, et al., "Yeast expressing hepatitis B virus surface antigen determinants on its surface: implications for a possible oral vaccine", Vaccine, Butterworth Scientific., Guildford, GB, XP004057292, Apr. 1, 1996, vol. 14, No. 5, pp. 383-388.
Warzecha et al, Journal of Virology, 2003, vol. 77, No. 16, pp. 8702-8711.
Breinig et al, FEMS Immunology and Medical Microbiology, 2003, vol. 38, pp. 231-239.
Biemelt et al, Journal of Virology, 2003, vol. 77, No. 17, pp. 9211-9220.
Sasagawa, et al., Virus Research, 2005, vol. 110, pp. 81-90.
Sasagawa, et al., Virology, 1995, vol. 206, pp. 126-135.
Kong et al, PNAS, 2001, vol. 98, No. 20, pp. 11539-11544.
Rose, et al, Journal of Virology, 1993, vol. 67, No. 4. pp. 1936-1944.
Kimbauer et al, Journal of Virology, 1993, vol. 67, No. 12, pp. 6929-6936.
Kaulsky et al., N. Engl. J. Med., 2002, vol. 347, No. 21, pp. 1645-1651.
Hagensee et al, Virology, 1995, vol. 206, pp. 174-182.
Balmelli et al, Journal of Virology, 1998, vol. 72, No. 10, pp. 8220-8229.
Takagi et al, PNAS, 2005, vol. 29, p. 17525-17530.
Tacket et al, The Journal of Infectious Diseases, 2000, vol. 182, p. 302-305.
Bryan Vaccine, 2007, vol. 25, p. 3001-3006.
Adams et al. Vaccine, 2007, vol. 25, p. 3007-3013.
Chan et al. Journal of Clinical Oncology, 2007, vol. 25, p. 2975-2982.
Sasagawa et al. Virus Research, 2005, vol. 110, p. 81-90.
Sasagawa et al, Virology, 1995, vol. 206, p. 126-135.

* cited by examiner

*Primary Examiner* — Agnieszka Boesen
(74) *Attorney, Agent, or Firm* — Oblon, Spivak, McClelland, Maier & Neustadt, L.L.P.

(57) ABSTRACT

The object of the present invention is to provide an edible vaccine which is effective for human papilloma virus (HPV) type 16 and available in large amounts inexpensively. An edible human papilloma virus vaccine obtained by culturing a transformant of an avirulent fission yeast host, wherein the transformant carries a gene encoding an antigenic protein of human papilloma virus introduced therein and accumulates the expressed antigenic protein in it.

19 Claims, 5 Drawing Sheets
(1 of 5 Drawing Sheet(s) Filed in Color)

HUMAN PAPILLOMAVIRUS VACCINE FOR ORAL ADMINISTRATION

TECHNICAL FIELD

The present invention is an edible vaccine effective against human papilloma virus (sometimes hereinafter referred to simply as "HPV").

BACKGROUND ART

HPV is a small del DNA virus having an icosahedral structure and no envelope. The genome of the virus contains open reading frames (ORFs) called E1-E7 and L1 and L2: "E" means early, and "L" means late. L1 and L2 encode capsid proteins of the virus. The early (E) genes are associated with functions such as virus replication and cell transformation. The L1 protein is the major capsid protein having a molecular weight of from 55 to 60 kDa when measured by polyacrylamide gel electrophoresis. The L2 protein is the minor capsid protein which also has an estimated molecular weight of from 55 to 60 kDa and an apparent molecular weight of from 75 to 100 kDa.

Although the mortality from cervical cancer has recently decreased in developed countries, it is the fifth leading cause of malignancy deaths and the second most common malignancy in women worldwide. Certain sexually transmitted types of HPV are the most important risk factor for cervical cancer. Recent reports show that from 30 to 50% of young women who recently had their first sexual intercourse have HPV infection in the cervix. Surprisingly, most cervical HPV infections are caused by high-risk types of HPV which can induce cancer. HPV types 16, 18, 31, 33, 35, 39, 45, 51, 52, 56, 58, 67 and 68, possibly some other types as well, are considered to be high-risk types.

This alarmingly high prevalence of HPV infection among young women suggests that educational and social health programs aimed at preventing of HPV infection may not be sufficiently effective in combating cervical cancer. Especially, prevention of infection with high-risk types of HPV is a priority for women in developing countries and young women who have not had uterine cervical cancer screening. The current cytologic screening (uterine cervical cancer screening) and post-onset cancer treatment are not cost-effective choices. Nationwide use of prophylactic vaccines against high-risk types of HPV can decrease the incidence of cervical cancer. It is estimated that even single use of a HPV16 vaccine decreases cervical cancer by half.

In pursuit of development of HPV vaccines, it was reported that high-level production of the HPV11 L1 protein led to the assembly of virus-like particles (hereinafter sometimes referred to simply as "VLPs") in an insect cell system (non-patent document 1). Successful synthesis of HPV16 VLPs in this insect cell system was also reported (non-patent document 2).

Later, we succeeded in production of HPV6- and HPV16- derived VLPs in the fission yeast *Schizosaccharomyces pombe* (hereinafter sometimes referred to simply as "*S. pombe*") (non-patent document 3). Although the yield of VLPs from the fission yeast is less than that from the insect cell system, the expression system using the fission yeast confers advantages in large-scale production of virus-like particles (hereinafter sometimes referred to simply as "VLP") and safety of use in humans.

Koustsky et al. were the first to report that parenteral vaccination (by injection) with HPV16 VLPs conferred 100% protection against HPV16 infection in is women (non-patent document 4).

Unfortunately, the injectable HPV16-VLP vaccine is expensive because it requires advanced techniques and special facilities for its production and storage. In addition, repetitive injection vaccinations required for efficacy has limited feasibility and are impractical in developing countries with limited numbers of trained members in their clinical staffs. Furthermore, it has been reported that injection vaccination with VLPs is a poor inducer of secretory IgA, which plays a major role in mucosal immunity (non-patent document 5). Immunization of the mucosa-associated lymphoid tissue (MALT), which is an immune tissue located in the respiratory and the digestive tract, can protect against viruses such as HPV that cause infections in the uterine and the vaginal mucosal epithelia. Balmelli et al. succeeded in inducing mucosal antibodies that neutralize HPV16 in the vagina by intranasal administration of HPV16-VLPs (non-patent document 6).

However, intranasal vaccination is also problematic like injection vaccination, because it requires preparation of relatively large amounts of purified HPV-VLPs. Stimulation of the gut-associated lymphoid tissue (GALT) with edible human papilloma virus vaccines (hereinafter sometimes referred to simply as "edible HPV vaccines") was attempted to induce strong mucosal immunity in the vagina. Two groups have produced edible HPV vaccines from tobacco and potato plants that express the HPV11 (non-patent document 7) and HPV16 (non-patent document 8) L1 genes.

Purification of HPV virus-like particles (HPV-VLPs) was disclosed in patent document 1. Patent documents 2-4 and patent document 5 disclose HPV vaccine preparations from expression systems in baculovirus and in insect cells, respectively. A nucleic acid vaccine for immunotherapy of HPV was also disclosed (patent document 6).

A therapeutic microorganism delivery system using non-vaccine active ingredient was also reported (patent document 7).

Patent Document 1: JP-A-2003-520188
Patent Document 2: JP-A-2001-519161
Patent Document 3: JP-A-2002-516291
Patent Document 4: JP-A-2002-510976
Patent Document 5: JP-A-2004-269
Patent Document 6: JP-A-2004-121263
Patent Document 7: JP-A-10-506791
Non-patent Document 1: Rose R C, et al. J Virol. 1993; 67: 1936-44.
Non-patent Document 2: Kirnbauer R, et al. J Virol. 1993; 67: 6929-36.9
Non-patent Document 3: Sasagawa T, et al. Virology. 1995; 206:126-35.
Non-patent Document 4: Koutsky L A, et al. N Engl J Med. 2002; 347: 1645-51.
Non-patent Document 5: Hagensee M E, et al. Virology 1995; 206: 174-82.
Non-patent Document 6: Balmelli C, et al. J Virol 1998; 72: 8220-9.
Non-patent Document 7: Warzecha H, et al. J Virol. 2003; 77: 8702-11.
Non-patent Document 8: Biemelt S, et al. J Virol. 2003; 77: 9211-20.

DISCLOSURE OF THE INVENTION

Problems that the Invention is to Solve

The object of the present invention is to provide an edible HPV vaccine which is available in large amounts inexpensively.

Means for Solving the Problems

The present inventors pursued their research for solutions to the above-mentioned problems by examining usefulness of a recombinant fission yeast expressing HPV proteins as a vaccine and have accomplished the present invention.

The present invention provides the following:

1. An edible human papilloma virus vaccine obtained by culturing a transformant of an avirulent fission yeast host, wherein the transformant carries a gene encoding an antigenic protein of human papilloma virus introduced therein and accumulates the expressed antigenic protein in it.
2. The vaccine according to 1, wherein the avirulent fission yeast host is Schizosaccharomyces pombe.
3. The vaccine according to 1 or 2, wherein the human papilloma virus is human papilloma virus type 16 (HPV16).
4. The vaccine according to 1, 2 or 3, wherein the gene encoding an antigenic protein is a gene encoding a capsid protein of the human papilloma virus.
5. The vaccine according to 4, wherein the capsid protein of the human papilloma virus is the L1 protein.
6. The vaccine according to 4 or 5, wherein the capsid protein of the human papilloma virus is the L1 protein of human papilloma protein type 16 (HPV16-L1).
7. The vaccine according to 4, 5 or 6, wherein the protein accumulated in the transformant is assembled into virus-liked particles.
8. The vaccine according to any one of 1 to 7, wherein the vaccine is a freeze-dried preparation of the transformant.

Effects of the Invention

Immunization with the edible HPV vaccine, especially the edible HPV16 vaccine, of the present invention and intranasal immunization with HPV-VLPs were observed to induce IgG in serum and the vagina and IgA in the vagina. All the induced antibodies strongly reacted with the HPV-VLP antigen. This indicates that the edible HVP16 vaccine is effective as a prophylactic vaccine against HPV16.

BRIEF EXPLANATION OF THE DRAWINGS

The patent or application file contains at least one drawing executed in color. Copies of this patent or patent application publication with color drawing(s) will be provided by the office upon request and payment of the necessary fee.

EXPLANATION OF REFERENCE SIGNS

Figure 4:
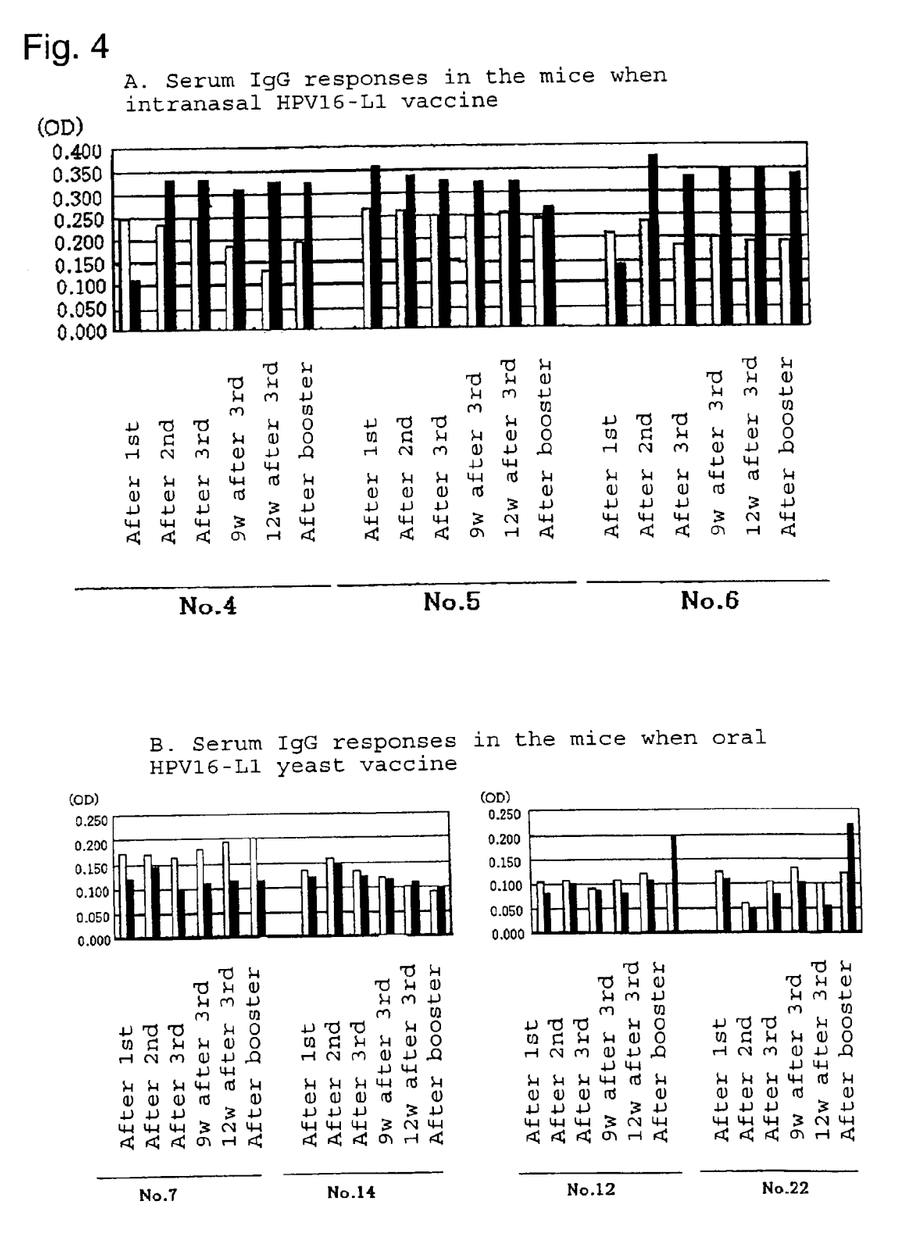
FIG. 4 Change in antibody responses to immunization HPV16 vaccines followed by intranasal boosting with HPV16-VLPs (Test Example 5)
Figure 5:
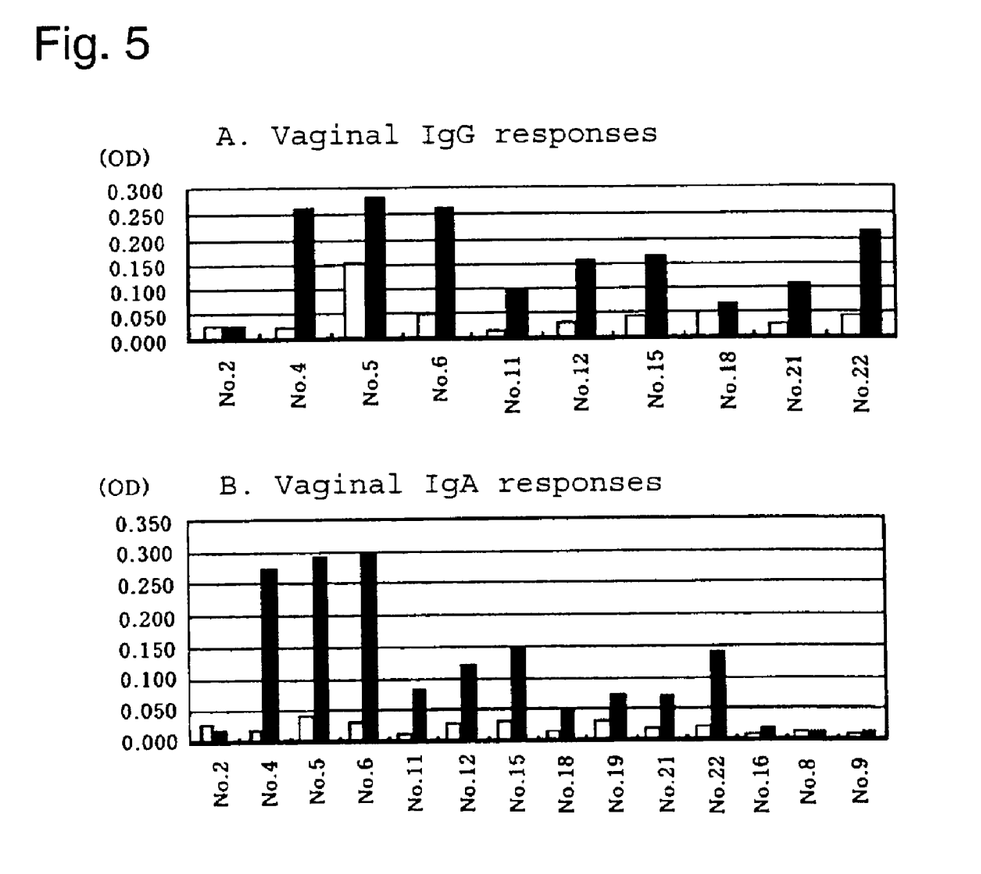
FIG. 5 Changes in antibody responses to immunization with HPV16 vaccines followed by intranasal boosting with HPV16-VLPs (Test Example 5)

☐ Reaction with denatured HPV16-L1 antigen (FIGS. 4 and 5)

■ Reaction with HPV16-VLP antigen (FIGS. 4 and 5)

BEST MODE FOR CARRYING OUT THE INVENTION

The present invention provides a cultured transformant which carries a gene encoding an antigenic protein of HPV and expresses and accumulates the protein, as an edible HPV vaccine.

In the present invention, the host into which a gene encoding an antigenic protein of HPV is introduced to obtain the transformant is an avirulent fission yeast, specifically the fission yeast S. pombe.

In the present invention, "the antigenic protein of HPV" specifically means a capsid protein of HPV, preferably L1. In the present invention, the HPV is preferably a high-risk type of HPV with the danger of cervical cancer, specifically HPV16.

In the present invention, any inducible expression vector for S. pombe into which a foreign gene is inserted, such as multicloning vectors disclosed in JP-A-7-163373 and JP-A-11-192094, may be used to introduce a gene encoding an antigenic protein of HPV into the host S. pombe without any restrictions. For example, a vector having a HPV16-L1 gene insert under the control of a thiamine-repressible promoter may be used to synthesize virus-like fragments recombinantly (non-patent document 3). The presence of the 55-kDa L1 protein in the virus-like fragments can be confirmed by Western blotting or the like.

In the present invention, "the transformant which accumulates an antigenic protein of HPV in it" is a transformant of an avirulent fission yeast host which accumulates the antigenic protein of HPV, and there are any particular restrictions. Specifically speaking, the transformant (hereinafter referred to "recombinant S. pombe") is cultured at 23 to 37° C. for 6 to 192 hours in a known culture medium, preferably YPD medium under appropriate conditions to accumulate the expressed antigenic protein of HPV in it. After culturing, the culture medium containing the recombinant S. pombe is centrifuged under appropriate conditions, for example, at 0 to 50° C. for 1 to 60 minutes at an acceleration of 500-3000 g, to collect the precipitate before oral administration.

The centrifugally collected recombinant S. pombe is called a yeast pellet and may be used as the "transformant which accumulates an antigenic protein of HPV in it" of the present invention. The yeast pellet may be processed appropriately, if necessary, for example, by freeze-drying, and the "transformant which accumulates an antigenic protein of HPV in it" of the present invention covers such a processed pellet. Freeze-drying may be carried out under ordinary conditions, for example, at a maximum shelf temperature of −20° C. overnight, though there are no particular restrictions as long as S. pombe is freeze-dried. The edible HPV vaccine of the present invention covers a transformant having accumulated an antigenic protein of HPV thus obtained.

Oral immunization has some advantages over prophylactic immunization through other routes. For example, edible vaccines are readily administered and acceptable to vaccine recipients. In addition, edible vaccines may contain active ingredients at lower concentrations than injection vaccines and therefore, can be produced at low production costs.

The edible HPV vaccine of the present invention may be formulated into preparations with at least one medicinally acceptable additional ingredient such as a carrier, a diluent, an adjuvant and/or a buffer. Further, the edible HPV vaccine of the present invention may be used as a mixture with food or the like. Known adjuvants such as an E. coli-derived mucosal adjuvant LT (R192) may be used.

The edible HPV vaccine of the present invention is administered at a dose of yeast (on a wet basis) selected within the range of from 10 to 500 mg/kg, preferably from 20 to 200 mg/kg, or at a dose of the HPV16-L1 protein selected within the range of from 0.05 to 5 mg/kg, preferably from 0.1 to 2 mg/kg. The edible HPV vaccine may be administered only once or repeatedly.

It is suggested that the edible HPV vaccine of the present invention is useful as a prophylactic vaccine against HPV16. The edible HPV vaccine of the present invention may be co-administered with conventional injection HPV vaccines and/or intranasal HPV vaccines in ordinary vaccination regimens for them, for example, as "a concomitant vaccine" to be used in combination with known vaccines. It may also be used as a "booster vaccine" to keep induced antibody titers.

EXAMPLES

Now, the present invention will be described by referring to Examples and Comparative Examples. However, the Examples are mere embodiments of the present invention which help reproduction of the present invention and by no means limits or restricts the present invention.

Example 1

Construction of Recombinant S. pombe Strain Expressing the HPV16-L1 Protein

A recombinant S. pombe strain was obtained in accordance with non-patent document 3. In order to increase L1 gene expression, the HPV16-L1 gene (B27; wild-type HPV16) was inserted into a new vector, pTL2M (JP-A-7-163373). The recombinant S. pombe strain was cultured in 2 L of YPD medium to allow the expression of the HPV16-L1 protein. It was confirmed by Western blotting that the recombinant S. pombe (pTL2-HPV16-L1) expressed high levels of the 55-kDa L1 protein. It was confirmed by electron microscopy that the expressed protein assembled into virus-like particles.

The total amount of the proteins expression by the yeast was about 10% of the wet weight of the yeast and about 50% of the freeze-dried yeast, and the L1 protein accounted for from 5 to 10% of the expressed proteins.

Example 2

Purification of Inactivated Freeze-Dried Yeast for Vaccine Preparation

A recombinant S. pombe strain was cultured in 2 L of YPD medium and collected by centrifugation at 4° C. for 10 minutes at 2000 g. The yeast pellet was washed with phosphate buffered saline (PBS) and resuspended in PBS at. 150 mg/mL on a wet basis. The S. pombe suspension was freeze-dried overnight at a maximum shelf temperature of −20° C. The freeze-dried recombinant S. pombe was sealed in air-tight plastic tubes and stored at 4° C. until use. The resulting edible vaccine is referred to as "HPV16-L1 yeast" for the sake of simplicity.

The freeze-dried HPV16-L1 yeast was resuspended in more than ten volumes of 70% ethanol in water and incubated at 4° C. for 30 minutes, in order to inactivate the yeast, then separated by filtration and dried, before use as an edible vaccine. Separate aliquots of the freeze-dried S. pombe strain was treated with ethanol similarly before oral administration. Further, "fresh-live yeast cells" were treated with ethanol similarly before oral administration.

Example 3

Vaccines for Study on Yeast Digestion in the Mouse Digestive Tract

A recombinant S. pombe strain expressing a red fluorescent protein (RFP) was obtained in the same manner as in Example 1. The recombinant S. pombe strain was cultured as described above to allow it to express the two proteins. After culturing, the yeast strain was centrifuged at 4° C. for 10 minutes at 2000 g, and the yeast pellet was collected.

Example 4

Adjuvant

The Escherichia coli heat-labile toxin LT (R192G), provided in accordance with Curr Top Microbiol Immunol 1999; 236: 216-36, was used as a mucosal adjuvant. The powdery adjuvant was suspended in PBS and stored at −30° C. until use.

Comparative Example 1

Purification of HPV16-VLPs for Intranasal Immunization

The HPV16-VLP protein was purified from the recombinant S. pombe, pTL2-HPV16-L1, obtained in Example 1 was purified by cesium chloride gradient ultracentrifugation (Giga-Hama Y, et. Biotechnology (N.Y.), 1994; 12: 400-4).

The cells were centrifuged at 4° C. at 2000 g for 5 minutes, resuspended in 50 mM potassium phosphate buffer [50 mM $KH_2PO_4$ (pH 6.5) containing 20 mM ethylenediaminetetraacetic acid (EDTA) and cooled on ice. The suspension was centrifuged again, and the yeast pellet was resuspended in 10 ml KKC buffer [20 mM $KPO_4$ (pH 6.5), 800 mM KCl, 0.1 mM $CaCl_2$, 1.5 mM $MgCl_2$ containing 5 mg/ml Novozyme] and incubated at 32° C. for 30 minutes to digest the yeast cell walls, and sonicated at for 1 minute at 60 W. The cell extract was recovered by centrifugation at 4° C. for 10 minutes at 7000 g. The pellet was resuspended in 10 mL VLP buffer (10 mM HEPES, 10 mM KCl (PH 7.0)) containing 0.5% surfactant (NP-40) and sonicated gently as previously mentioned.

The supernatant was collected and layered on 40% sucrose VLP buffer and centrifuged at 4° C. for 2 hours at 27000 g in a Beckman SW28 rotor (Beckman Coulter). The pellet was resuspended in VLP buffer and centrifuged at 4° C. for 20 hours at 27000 g in CsCl-equilibrated VLP buffer in the SW rotor. The appropriate fractions were diluted to a density of 1.29 g/ml and centrifuged at 4° C. for 2.5 hours at 27000 g.

The pellet was resuspended in VLP buffer and stored at −30° C.

The assembly of the HPV16-VLP protein was confirmed by enzyme-linked immunosorbent assay (ELISA) using two anti-HPV16 monoclonal antibodies, Camvir-5 and Camvir-6 (provided from Margaret Stanley, Cambridge University), which recognize conformation-dependent epitopes.

The HPV16-VLP protein was used for intranasal immunization. The intranasal vaccine is called "HPV16-VLP" for the sake of simplicity.

Test Example 1

Yeast Digestion in Mouse Digestive Tract

Four 9-week-old BALB/c mice were fed 20 mg (on a wet basis) of the fresh-live or freeze-dried yeast expressing a fluorescent protein (RFP) obtained in Example 3, 6 times at hourly intervals after 12 hours of starvation. After the final feed, the mice were dissected and examined for yeast digestion. The digestive tracts of the mice were cut, and touch smears were obtained on glass slides. Fluorescent yeast cells were observed on each slide under Axiovert S-100 Microscope (Carl Zeiss, Germany) and photographed with Fuji 3CCD camera (Fuji Film).

The fresh-live yeast cells were not digested because they were observed at most parts of the digestive tract and excreted in stools.

Figure 1:
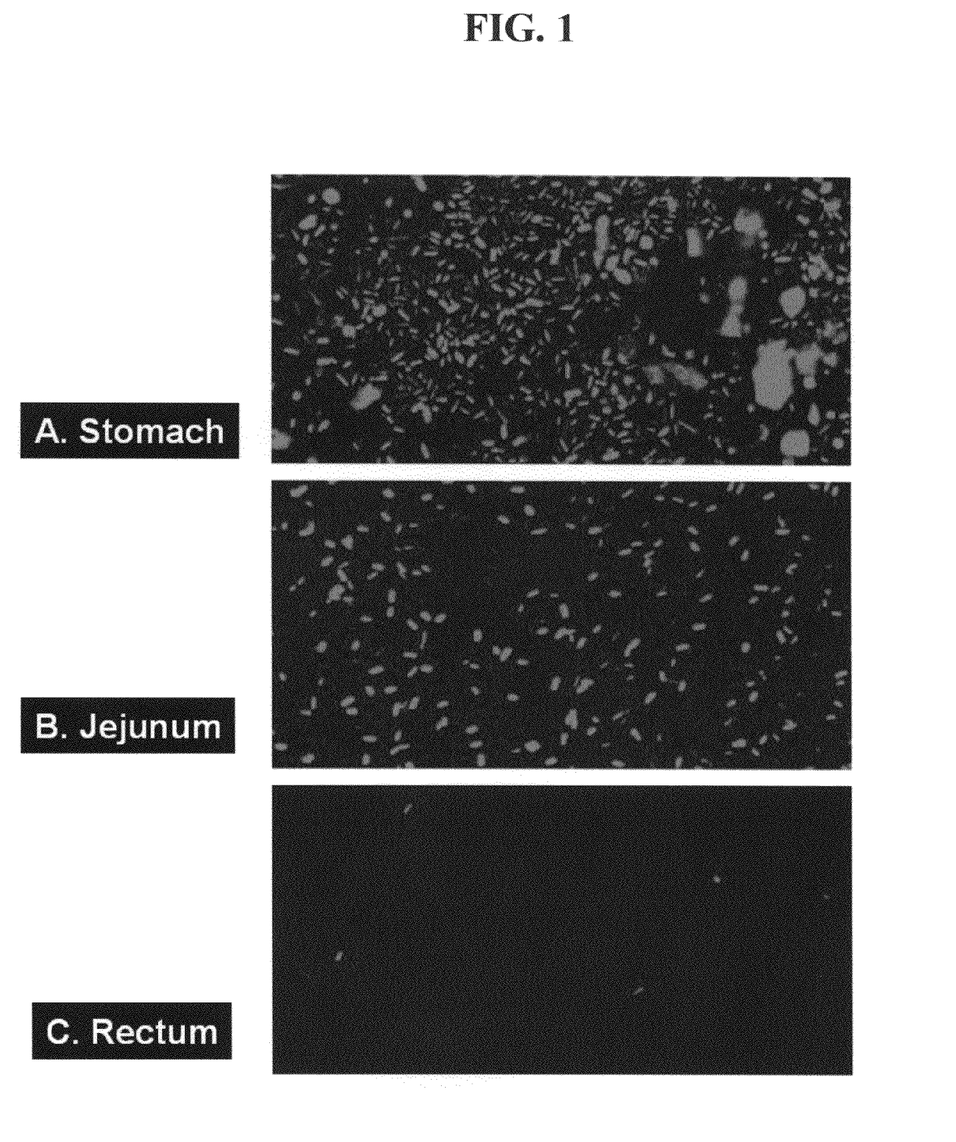
FIG. 1A Digestion of a freeze-dried yeast in the stomach (Test Example 1)
FIG. 1B Digestion of a freeze-dried yeast in the abdominal cavity (Test Example 1)
FIG. 1C Digestion of a freeze-dried yeast in the intestine (Test Example 1)

In contrast, the freeze-dried yeast cells were not disrupted in the stomach (FIG. 1A) or the jejunum (FIG. 1B), but cells decreased from the ileum to the large intestine and were very few in the rectum (FIG. 1C). This suggests that freeze-dried yeast cells are digested in the intestine where the gut-associated lymphoid tissue is located.

Test Example 2

Antibody Production induced by Edible Vaccine "HPV16-L1 Yeast"

Female 9-week-old BALB/c mice were fed the freeze-dried yeast suspended in PBS after 12 hours of starvation. The mice were divided into 6 groups as shown in Table 1 and vaccinated at 4-week intervals and examined for antibody production. Group 1 is a negative control, and Group 2 is a positive control. The doses are expressed on a wet basis.

TABLE 1

| | Mouse ID | Vaccine | Dose | Adjuvant | Vaccination route |
|---|---|---|---|---|---|
| Group 1 | Nos. 1-3 | Wild-type yeast | 50 mg | — | Oral |
| Group 2 | Nos. 4-6 | Purified HPV16-L1 | 5 µg | 10 µg | Intranasal |
| Group 3 | Nos. 7-9 | HPV16-L1 yeast | 50 mg | — | Oral |
| Group 4 | Nos. 10-12 | HPV16-L1 yeast | 50 mg | 10 µg | Oral |
| Group 5 | Nos. 13-18 | HPV16-L1 yeast | 150 mg | — | Oral |
| Group 6 | Nos. 19-24 | HPV16-L1 yeast | 150 mg | 10 µg | Oral |

After the vaccinations, serum samples and vaginal samples were collected from the mice. The serum samples were obtained from blood collected from the mouse tail, and the vaginal samples were obtained by washing the vaginae with 100 µl of PBS using a micropipette. To avoid the influence of the mouse estrous cycle on antibody production, the vaginal samples were collected twice with a 5-day interval, and the two samples were mixed and used for analysis. The samples were collected a few days before the first oral immunization and four weeks after each immunization. All the samples were divided into aliquots and stored at −30° C. until use to avoid repeated thawing.

Figure 2:
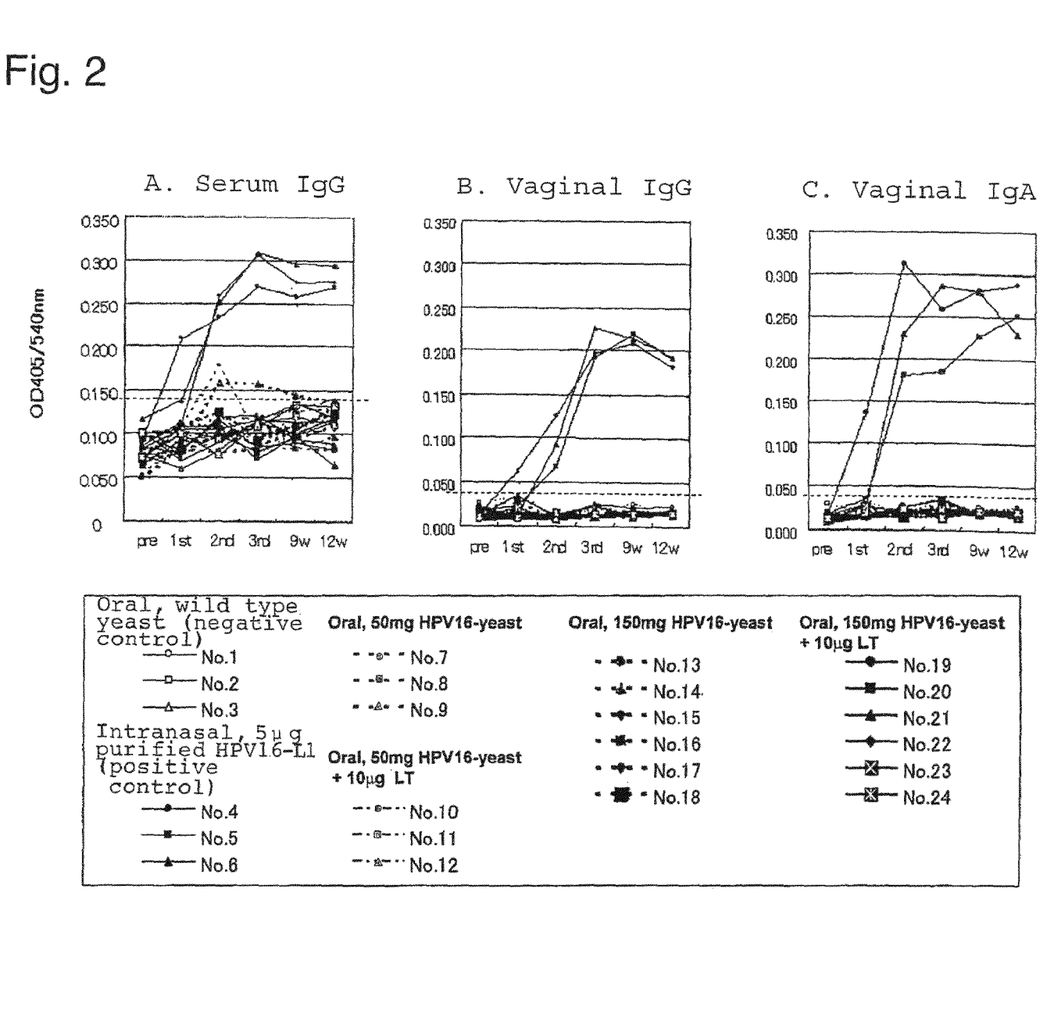
FIG. 2 Induction of antibodies by immunization with HPV16 vaccines (Test Example 2)

After three immunizations, the levels of HPV16-specific antibodies (IgG and IgA) were evaluated by ELISA (FIG. 2).

1) ELISA

HPV16-VLP protein purified from insect cells in accordance with Rose (J Virol. 1933; 67: 1936-44., J Gen Virol 1994; 75: 2445-9.) was used as the HPV16-VLP antigen for ELISA.

For antigen coating, 100 ng and 300 ng of HPV16-VLP antigen was incubated in PBS on ELISA plates (NUNC Immunoplate Maxisorp; Nalgene Nunc International) at 4° C. overnight.

The coated plates were washed with PBST (PBS, 0.1% Tween-20) once and incubated with blocking buffer (3% albumin, 0.5% FCS in PBST) at room temperature (RT; 20-24° C.) for 1 hour. All the subsequent washes were carried out with PBST.

In the antibody reaction, 1 µl of serum samples or 20 µl of vaginal samples were mixed with reaction buffer (1.5% bovine albumin, 0.25% FCS in PBST), added to the ELISA plates and incubated at room temperature for 3 hours.

After three washes, a biotinylated anti-mouse IgA or IgG antibody (diluted with the reaction buffer at a ratio of 1:1500 for IgA and 1:1000 for IgG) was added to the plates and incubated at room temperature for 1 hour.

After three washes, 100 µl of strepavidin-horseradish conjugate (DAKO, Germany) diluted with PBST at a ratio of 1:5000 was added to the plates and incubated for 30 minutes.

After three washes, 100 µl of 50 mM citrate buffer (pH 5.0; 0.0075% hydrogen peroxide) containing one tablet of ABT [2,2'-azino-bis(3-ethylbenzeothiazoline-6-sulfonic acid) (Sigma) was added to the plates. After 1 hour of color development at room temperature, the optical density (OD) values were measured at dual wavelengths (405/540 nm) with an automated plate reader (Iems Reader MS; Labsystems). The final OD values were calculated by substraction of the OD values at 540 nm from those at 405 nm.

2) Evaluation

The cut-off points for IgA and IgG titers in serum were set at the average OD values plus 2.5 times the standard deviations of 10 serum and vaginal samples from non-immunized mice. ELISA was carried out in duplicate or more for each sample, and the mean OD values were used for evaluation. Two sets of positive and negative control samples were included in each experiment to compensate for inter-assay variation.

All the positive control mice showed high OD values for serum IgG, vaginal IgG and vaginal IgA, although no serum IgA responses were detected.

Finally, two of the 18 mice (11%) (No. 7 in Group 3 and No. 14 in Group 5) showed transient weak serum IgG responses after the second immunization (FIG. 2A). In contrast, no vaginal IgG or IgA responses were observed in any orally vaccinated mice (FIGS. 2B and 2C).

Test Example 3

Boosting of Immune Responses by Intranasal Administration of Purified HPV16-VLPs A suboptimal dose (1 µg) of the HPV16-VLP was intranasally administered as a booster to all the mice, including the positive controls, negative controls and those orally immunized with the HPV16-L1 yeast, 12 weeks after the final immunization.

Figure 3:
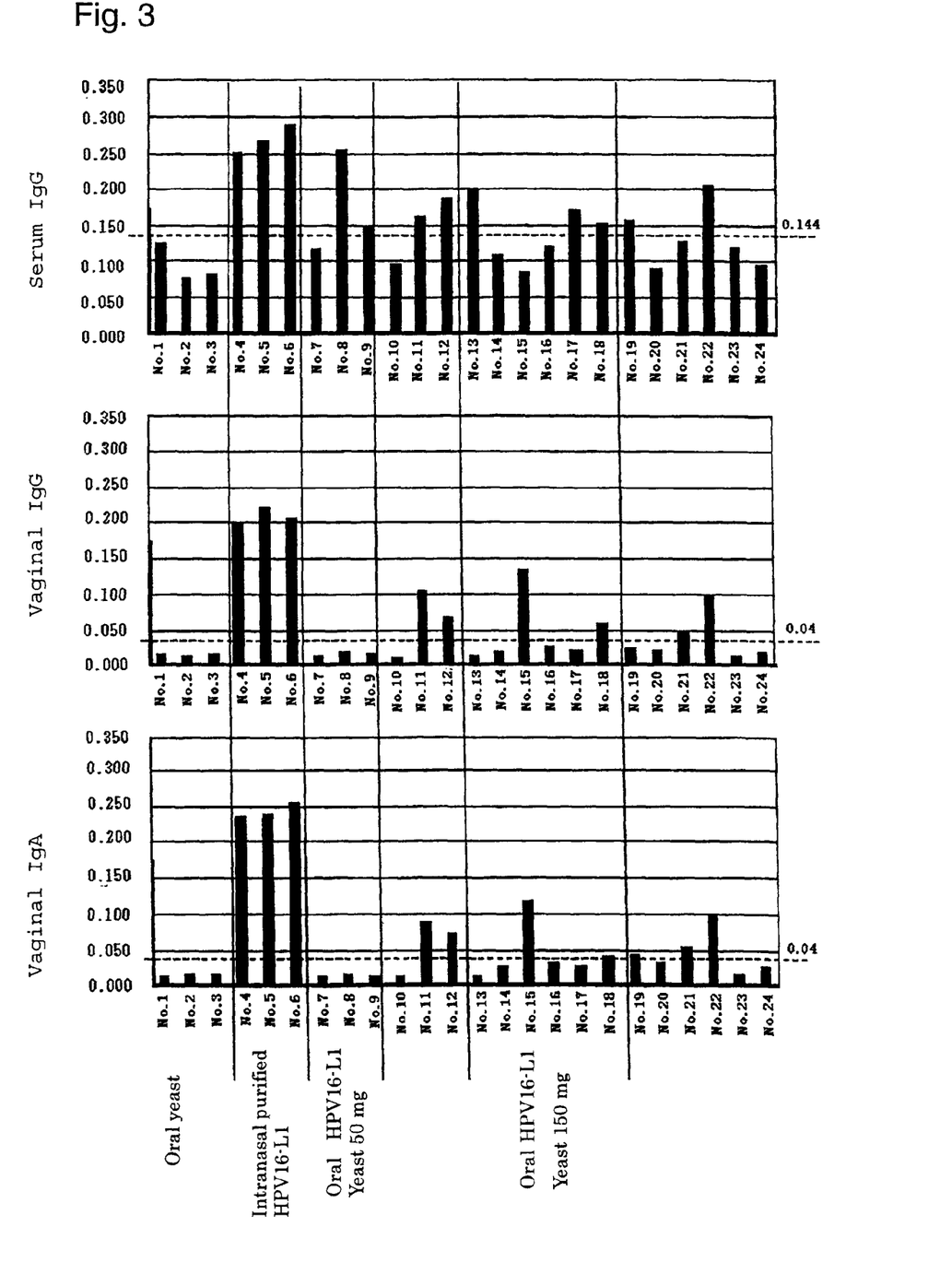
FIG. 3 Induction of antibodies by immunization with HPV16 vaccines followed by intranasal boosting with HPV16-VLPs Test Example 3)

The results are shown in Table 2 and FIG. 3.

TABLE 2

Titers of serum IgG and vaginal IgA induced in mice

| Mouse ID No. | Vaccination route 1st-3rd/4th | Antigen and dose Yeast | HPV16 VLP | Adjuvant | Antibody titer (dilution) Serum IgG | Vaginal IgG |
|---|---|---|---|---|---|---|
| No. 1 | Oral/Intranasal | Wt[a] 50 mg | 1 μg | | 0 | 0 |
| No. 2 | Oral/Intranasal | Wt 50 mg | 1 μg | | 0 | 0 |
| No. 4 | Intranasal/Intranasal | 0 | 5 μg + 1 μg | 10 μg | 6400 | 1600 |
| No. 5 | Intranasal/Intranasal | 0 | 5 μg + 1 μg | 10 μg | 25600 | 3200 |
| No. 6 | Intranasal/Intranasal | 0 | 5 μg + 1 μg | 10 μg | NA | NA |
| No. 7 | Oral/Intranasal | HPV16[b] 50 mg | 1 μg | — | NA[c] | 0 |
| No. 8 | Oral/Intranasal | HPV16 50 mg | 1 μg | — | 3200 | NA |
| No. 9 | Oral/Intranasal | HPV16 50 mg | 1 μg | — | 1600 | NA |
| No. 10 | Oral/Intranasal | HPV16 50 mg | 1 μg | 10 μg | NA | 0 |
| No. 11 | Oral/Intranasal | HPV16 50 mg | 1 μg | 10 μg | 1600 | 400 |
| No. 12 | Oral/Intranasal | HPV16 50 mg | 1 μg | 10 μg | 1600 | 800 |
| No. 13 | Oral/Intranasal | HPV16 150 mg | 1 μg | — | 1600 | NA |
| No. 15 | Oral/Intranasal | HPV16 150 mg | 1 μg | — | 1600 | 800 |
| No. 17 | Oral/Intranasal | HPV16 150 mg | 1 μg | — | 3200 | NA |
| No. 19 | Oral/Intranasal | HPV16 150 mg | 1 μg | 10 μg | 1600 | 100 |
| No. 21 | Oral/Intranasal | HPV16 150 mg | 1 μg | 10 μg | NA | 100 |
| No. 22 | Oral/Intranasal | HPV16 150 mg | 1 μg | 10 μg | 3200 | 800 |

[a]wild-type yeast, [b]HPV16-L1 yeast, [c]not detected
(Not applicable)

All the three positive controls (100%) and 9 orally vaccinated mice showed positive reactions for serum IgG four weeks later (FIG. 3A). In terms of vaginal IgG, the three positive controls (100%) and 6 orally vaccinated mice (33%) were positive, while none of the negative controls were positive (FIG. 3B). With respect to vaginal IgA, the three positive controls (100%) and 7 orally vaccinated mice (39%) were positive, and none of the negative controls were positive (FIG. 3C).

No antibodies were induced in the negative controls even by intranasal boosting with a suboptimal amount of HPV16-VLPs after oral yeast vaccination, whereas mice orally vaccinated with the HPV16-L1 yeast showed positive immune responses, which suggests that HPV16-specific immune responses can be primed by the HPV16-L1 yeast.

Test Example 4

Effects of Oral Doses of HPV16-L1 Yeast and Adjuvant on Immune Responses

The antibody-positive rates in the HPV16-L1 yeast-vaccinated mice did not differ at a low HPV16-L1 yeast dose (50 mg) and a high HPV16-L1 yeast dose (100 mg).

The mucosal adjuvant LT (R192G) was administered with the HPV16-L1 yeast to some mice to enhance the antibody response. The adjuvant did not cause serious side effects in mice. The adjuvant did not any difference in serum IgG responses among groups orally vaccinated with the HPV16-L1 yeast, while the positive rates were two-fold higher for vaginal IgG and 2.5-fold higher for vaginal IgA in the adjuvant groups than in the non-adjuvant groups, though there were no statistically significant differences. The OD values for vaginal IgA were slightly higher in the adjuvant group of HPV16-L1 yeast-vaccinated mice than in the non-adjuvant group of HPV16-L1 yeast-vaccinated mice (P=0.085; Mann-Whitney test), which suggest a slight effect of the adjuvant.

Example 5

Characterization of the Antibodies Elicited by Oral and Intranasal Vaccination

The reactivity of antibodies was assayed by ELISA using HPV16-VLP and denatured HPV16-L1 protein coatings.

HPV16-VLPs were boiled in bicarbonate buffer (100 g for IgG and 300 ng for IgA) for 10 minutes and used as the denatured HPV16-L1 protein antigen in the ELISA. The reactivities to the VLP antigen or the denatured HPV16-L1 antigen expressed in OD were compared. The sera and the vaginal washings were serially diluted, and the antibody titers were measured.

Previous studies demonstrated that antibodies that recognize conformation-dependent epitopes on HPV-VLPs neutralize the virus. Here, it was investigated whether the induced antibodies react more strongly to the HPV16-VLP antigen than to the denatured HPV16-L1 antigen.

The antibodies induced in two intranasally HPV16-VLP-vaccinated mice (No. 4 and No. 6) by the first intranasal immunization reacted more strongly with the HPV16-VLP antigen. However, the serum IgG antibodies induced at the second immunization or later reacted more strongly with the HPV16-VLP antigen (FIG. 4A). This indicates seroconversion from a non-specific type of reaction to a HPV16-specific type of reaction after the second immunization (FIG. 4A).

The antibodies induced in orally HPV16-L1 yeast-vaccinated mice after intranasal boosting (No. 12 and No. 12 and No. 22) reacted more strongly with the HPV16-VLP antigen (FIG. 4B).

In contrast, two mice orally vaccinated with the HPV16-L1 yeast were transiently positive but eventually negative after boosting. The antibodies in one (No. 7) of the two reacted more strongly with the denatured HPV16-L1 antigen, while the antibodies in the other (No. 14) reacted equally with both types of HPV16-VLP antigen throughout the time course of the experiment (FIG. 4B).

The results of the assays of vaginal samples from mice orally vaccinated with the HPV16-L1 yeast showed that IgG antibodies were elicited in 6 mice (FIG. 5A). The antibodies elicited in all these mice reacted more strongly with the HPV16-VLP antigen.

The edible HPV16-L1 yeast vaccine elicits HPV16-specific vaginal IgA and IgG antibodies, as well as serum IgG. Although oral administration of the freeze-dried HPV16-L1 yeast alone did not induce anti-HPV16 antibodies, but when it was followed by intranasal boosting with a suboptimal amount of HPV16-VLPs, serum IgG, vaginal IgG and vaginal IgA were elicited in 50%, 33% and 39% of the mice, respectively. In the negative control mice, no anti-HPV16 antibodies were elicited even after the same intranasal boosting. Intranasally administered HPV16-VLPs increased antibody production probably by enhancing the activity of primed memory B cells that recognize HPV16. All of the induced antibodies reacted more strongly with HPV16-VLP antigen than with the denatured HPV16-L1 antigen, which suggests that these antibodies recognize conformation-dependent HPV16-L1 epitopes and are neutralizing.

INDUSTRIAL APPLICABILITY

As described above, the edible HPV16-L1 yeast vaccine of the present invention induces neutralizing antibodies and is functional as a vaccine. Therefore, a vaccine is provided which is less painful for patients than intranasal vaccines and injectable vaccines to be used singly. The edible vaccine needs no purification and therefore, is available in large amounts inexpensively. The vaccine may be used in various ways, primarily to induce anti-HPV antibodies in unimmunized people, and also as a booster to keep induced antibody titers.

The entire disclosure of Japanese Patent Application No. 2004-263580 filed on Sep. 10, 2004 including specification, claims, drawings and summary is incorporated herein by reference in its entirety.

What is claimed is:

1. A method for orally priming a subject's immune system comprising:
    orally administering a freeze-dried recombinant *Schizosaccharomyces pombe* avirulent fission yeast that expresses or accumulates within it an exogenous protein of human papilloma virus to a subject in need thereof in an amount effective to induce an immune response against human papilloma virus.

2. The method of claim 1, wherein said freeze-dried recombinant *Schizosaccharomyces pombe* avirulent fission yeast comprises HPV virus-like particles (VLP).

3. The method of claim 1, wherein said freeze-dried *Schizosaccharomyces pombe* avirulent fission yeast contains an antigenic protein that is HPV L1 protein.

4. The method of claim 1, wherein said subject is a human infected with HPV16 and said freeze-dried *Schizosaccharomyces pombe* avirulent fission yeast contains an antigenic L1 protein from human papilloma virus type 16 (HPV16) that induces an immune response against HPV16.

5. The method of claim 1, wherein said freeze-dried *Schizosaccharomyces pombe* avirulent fission yeast further comprises an adjuvant.

6. The method of claim 1, further comprising administering a conventional HPV vaccine by injection or intranasal route.

7. The method of claim 1, wherein said freeze-dried *Schizosaccharomyces pombe* avirulent fission yeast comprises an isolated antigenic protein of human papilloma virus (HPV) which has been expressed by an avirulent fission yeast that is *Schizosaccharomyces pombe*.

8. The method of claim 1, wherein said freeze-dried *Schizosaccharomyces pombe* avirulent fission yeast comprises *Schizosaccharomyces pombe* that has expressed an antigenic protein of human papilloma virus (HPV).

9. The method of claim 1, comprising: orally administering to said subject a dose ranging from 10 to 500 mg/kg of a freeze-dried *Schizosaccharomyces pombe* avirulent fission yeast which has expressed an antigenic protein of human papilloma virus (HPV).

10. The method of claim 1, comprising orally administering to said subject a dose ranging from 0.05 to 5 mg/kg of HPV-16 L1 protein that is contained in a *Schizosaccharomyces pombe* avirulent fission yeast.

11. The method of claim 1, comprising orally administering multiple doses of an antigenic protein of human papilloma virus (HPV) which is contained in a *Schizosaccharomyces pombe* avirulent fission yeast.

12. The method of claim 1, wherein said freeze-dried recombinant *Schizosaccharomyces pombe* avirulent fission yeast has accumulated a recombinant antigenic protein of HPV within it.

13. The method of claim 12, wherein said recombinant *Schizosaccharomyces pombe* avirulent fission yeast has been cultured at 23 to 37° C. for 6 to 192 hrs under conditions that permit it to accumulate the expressed antigenic HPV antigenic protein.

14. The method of claim 1, further comprising intranasal boosting using said exogenous protein of human papilloma virus.

15. The method of claim 14, wherein the exogenous protein of human papilloma virus is HPV16-L1.

16. A method for orally priming a subject's immune system against subsequent exposure to a human papilloma virus antigen comprising:
    orally administering to a subject in need thereof a freeze-dried recombinant *Schizosaccharomyces pombe* avirulent fission yeast that expresses or accumulates within it an exogenous protein of human papilloma virus in an amount effective to prime the immune system of the subject against subsequent exposure to said protein of human papilloma virus.

17. The method of claim 16, wherein the endogenous protein of human papilloma virus is HPV16-L1.

18. The method of claim 16, wherein subsequent exposure of said subject to the exogenous protein of human papilloma virus induces an antibody response against HPV.

19. A method for inducing antibodies to HPV comprising:
    orally priming a subject's immune system with a priming antigen, and
    boosting the primed subject with the priming antigen;
    wherein said priming antigen comprises a freeze-dried recombinant *Schizosaccharomyces pombe* avirulent fission yeast that expresses or accumulates within it an exogenous protein of human papilloma virus.

* * * * *